United States Patent
Ganey et al.

(10) Patent No.: US 11,925,532 B2
(45) Date of Patent: Mar. 12, 2024

(54) VENTED WOUND DRESSING BARRIER

(71) Applicant: Vivex Biologics Group, Inc., Atlanta, GA (US)

(72) Inventors: Timothy Ganey, Tampa, FL (US); Shabnam Namin, Miami, FL (US); Hanna Kaliada, Miami, FL (US); Santiago Osorio, Hollywood, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 130 days.

(21) Appl. No.: 17/547,790

(22) Filed: Dec. 10, 2021

(65) Prior Publication Data

US 2023/0181372 A1  Jun. 15, 2023

(51) Int. Cl.
  *A61F 13/00* (2006.01)
  *A61L 15/40* (2006.01)
  *A61L 27/36* (2006.01)
  *B05D 3/00* (2006.01)
  *C12N 5/073* (2010.01)

(52) U.S. Cl.
  CPC .. *A61F 13/00034* (2013.01); *A61F 13/00012* (2013.01); *A61F 13/00017* (2013.01); *A61F 13/00029* (2013.01); *A61F 13/00995* (2013.01); *A61L 15/40* (2013.01); *A61L 27/3604* (2013.01); *B05D 3/007* (2013.01); *C12N 5/0605* (2013.01); *A61F 2013/00314* (2013.01); *A61K 2800/84* (2013.01); *C12N 2533/92* (2013.01)

(58) Field of Classification Search
  None
  See application file for complete search history.

(56) References Cited

U.S. PATENT DOCUMENTS

| | | | |
|---|---|---|---|
| 2,877,765 A * | 3/1959 | Bunyan | A61F 13/00021 602/47 |
| 5,255,587 A | 10/1993 | Eichenberg et al. | |
| 5,356,356 A | 7/1994 | Hildebrandt et al. | |
| 6,626,965 B2 | 9/2003 | Workman et al. | |
| 8,323,701 B2 | 12/2012 | Daniel et al. | |
| 8,858,647 B2 | 10/2014 | Markman | |
| 10,143,777 B2 | 12/2018 | LeVaughn et al. | |

(Continued)

FOREIGN PATENT DOCUMENTS

| | | |
|---|---|---|
| EP | 0399782 | 4/1991 |
| WO | 9310722 | 6/1993 |

(Continued)

*Primary Examiner* — Allison M Fox
(74) *Attorney, Agent, or Firm* — David L. King

(57) ABSTRACT

A vented wound dressing barrier includes one or more membrane layers with a plurality of vents. The vents are cut along a perimeter of the vents through the one or more membrane layers. Each vent having a connection portion uncut relative to the one or more membrane layers thereby forming a hinge configured to allow the vents to open for drainage when exposed to fluid underlying the vented wound dressing barrier. The plurality of vents is each cut along the perimeter without removal of any of the membrane layer. The one or more membrane layers with the plurality of vents has a surface for covering a wound, the surface area in the absence of a fluid pressing on the vents having no openings or voids which reduce the surface area of a vented wound dressing barrier area covering a wound.

14 Claims, 9 Drawing Sheets

(56) References Cited

U.S. PATENT DOCUMENTS

| | | |
|---|---|---|
| 10,898,312 B2 | 1/2021 | Wirth et al. |
| 11,058,530 B2 | 7/2021 | Chen et al. |
| 2004/0260315 A1* | 12/2004 | Dell ...................... A61F 2/0063 |
| | | 623/23.72 |
| 2013/0084323 A1* | 4/2013 | Riebman ............. A61L 26/0042 |
| | | 530/356 |
| 2018/0043058 A1 | 2/2018 | Kheradvar |
| 2019/0091371 A1 | 3/2019 | LeVaughn et al. |
| 2019/0134268 A1 | 5/2019 | Malinin |
| 2019/0269815 A1 | 9/2019 | Williams et al. |
| 2021/0393852 A1 | 12/2021 | McQueen et al. |

FOREIGN PATENT DOCUMENTS

| | | |
|---|---|---|
| WO | 9706837 | 2/1997 |
| WO | 2012112417 | 8/2012 |

* cited by examiner

VENTED WOUND DRESSING BARRIER

TECHNICAL FIELD

The present invention relates to a vented wound dressing barrier, more particularly, to a wound dressing having one or more membrane layers with vents to enhance or facilitate the drainage of fluids.

BACKGROUND OF THE INVENTION

Wounds often seep fluids as part of the edema.

Physicians typically accommodate drainage and wound vacuum procedures using techniques that might include: quilting, leaving egress for fluid edema build up, expanded fenestrations, or perforations. In U.S. Pat. No. 9,272,003 B2 entitled, "Placental Tissue Grafts" issued Mar. 1, 2016, to John Daniel et al. describes using perforations in the form of holes to achieve blood flow passages. These holes by their very nature reduce the surface area of the placental tissue graft, diminish barrier function, and proportionately lessen inherent factors that are prescriptive to wound protection. Although supporting a province of drainage, this adversely loses the beneficial healing aspects of this membrane layer to provide coverage and prevent desiccation. Also, the single layer placental tissue is very weak and fragile, so the addition of holes or fenestrations weakens an already fragile tissue.

Loss of tissue aside, these techniques create inefficiency in piecing together a wound dressing due to the tissue's fragile nature resulting in tears and the absence in areas to the beneficial healing factors. Perforations or holes remove healing constituents in the tissue matrix, and this is undesirable.

The present invention described hereinafter provides drainage without any losses of material.

SUMMARY OF THE INVENTION

A vented wound dressing barrier includes one or more membrane layers with a plurality of vents. The vents are cut along a perimeter of the vents through the one or more membrane layers. Each vent having a connection portion uncut relative to the one or more membrane layers thereby forming a hinge configured to allow the vents to open for drainage when exposed to fluid underlying the vented wound dressing barrier. The plurality of vents is each cut along the perimeter without removal of any of the membrane layer. The one or more membrane layers with the plurality of vents has a surface for covering a wound, the surface area in the absence of a fluid pressing on the vents having no openings or voids which reduce the surface area of a vented wound dressing barrier area covering a wound.

In one embodiment, the vented wound dressing barrier has a base layer underlying and attached to an inner surface of one of the one or more membrane layers. The base layer has a plurality of holes, the plurality of holes being aligned, partially aligned or staggered with respect to the plurality of vents. The holes of the base layer are sized smaller than the cut perimeter of the vents. The vents of the one or more membrane layers overly the holes of the base layer and the base layer forms a lip preventing the vents from opening inwardly relative to a wound being dressed, serving functional similarity to a flap valve.

In another embodiment, the vented wound dressing barrier has one or more synthetic or electrospun fabric layers attached to the one or more membrane layers. The one or more synthetic or electrospun fabric layers having a plurality of vents aligned, partially aligned or staggered with the vents of the one or more membrane layers configured to open with the vents of the one or more membrane layers to allow drainage of fluids from a wound without regard to common conduit described by geometric alignment or singular and consecutive venting.

The vented wound dressing barrier further has one or more combinations of chitosan, polymer-based, collagen dressings, hydrocolloids, hydrogels, fibers, gauze, alginates, foams, matrix elaborations including hyaluronic acid, cell-matrix combinations, matrix-exosome combinations, matrix-secretome combinations, infusions, perfusions, and other topical wound dressings intended to cover surface wounds of varying depths.

In another embodiment, the vented wound dressing barrier is cryoprotected, bioprotected, freeze-dried, air-puffed, thermally imbued with at-melting point modification, embossed, channeled, or in other ways have topographical modifications inherent to individual lamina or in register combine to create hollowed or microfluidic conduits between layers. In one embodiment, at least one of the one or more membrane layers is a placental tissue membrane. The one or more membrane layers with a plurality of vents are multiple membrane layers of amnion or chorion or combinations of amnion and chorion layers stacked to form a multi-layered laminate. The plurality of vents are oriented and arranged in patterns or are oriented in random orientations. The plurality of vents can be made in random sizes or shapes in the one or more membrane layers. The random shapes can be one or more of a crescent, rhomboid, triangular, round or elliptical shape.

In one embodiment, the vented wound dressing barrier further has a cryoprotectant coating. The cryoprotectant coating covering the one or membrane layers and wherein the combination of the one or more membrane layers with the cryoprotectant coating are dried or freeze-dried to form a dried or freeze-dried coated vented wound dressing barrier.

The cryoprotectant is preferably a polyampholyte tissue protectant and is non-toxic. The coating provides a reduction in inflammation at the wound site and enhances healing of the wound. The coating need not and preferably is not washed away when the membrane layers are rehydrated for use in a wound dressing.

In the above described vented wound dressing barrier, the product is produced by the method of making a vented wound dressing barrier with the steps of: providing one or more membrane layers and cutting a plurality of vents using a cutting die pressed into the one or more membrane layers wherein each vent is cut along a perimeter with an uncut portion of the vent forming a hinge to allow the vent to open for drainage of fluid underlying the vented would dressing barrier.

In embodiments where the one or more membrane layers has a plurality of layers, the method further has the step of stacking the plurality of layers to form a laminated structure prior to cutting the vents.

In other embodiments where the one or more membrane layers has a plurality of layers, the method further has the step of staggering the stacking of the plurality of layers to form a laminated structure prior to cutting the vents, wherein the openings are unaligned or at least partially aligned and do not form what would be a common conduit were they all hinged open simultaneously.

The method further has the step of coating the one or more layers in a cryoprotectant of polyampholyte either singularly or successively and then drying or freeze-drying to form a dried or freeze dried coated one or more membrane layers.

In another embodiment a coated wound dressing barrier has one or more membrane layers and a cryoprotectant coating. The cryoprotectant coating covers the one or membrane layers and the combination of the one or more membrane layers with the cryoprotectant coating can be dried or freeze-dried to form the coated wound dressing barrier. The cryoprotectant of the coated wound dressing barrier can be a polyampholyte tissue protectant.

BRIEF DESCRIPTION OF THE DRAWINGS

The invention will be described by way of example and with reference to the accompanying drawings in which.

DETAILED DESCRIPTION OF THE INVENTION

Figure 1A:
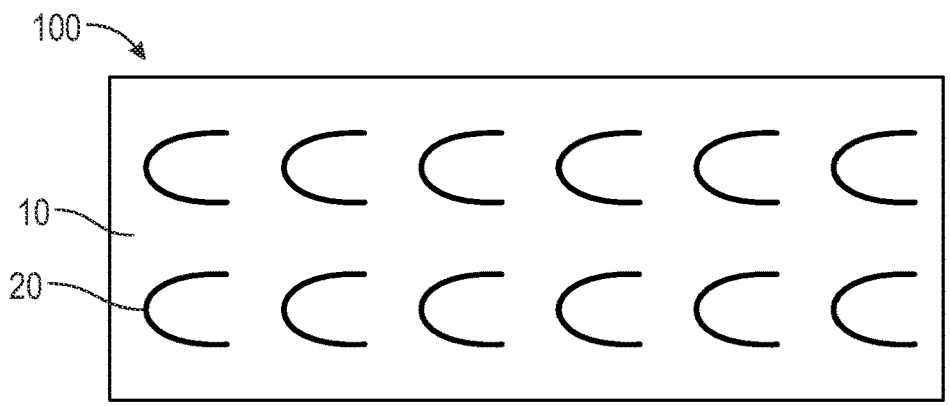
FIG. 1A is a perspective view of an exemplary vented wound dressing barrier of the present invention in a square or rectangular shape with a plurality of arcuate cut vents or vent openings.

With reference to FIGS. 1A-9, various embodiments of the vented wound dressing barrier according to the present invention are illustrated. With reference to FIGS. 10A and 10B, a die for fabricating vents in the vented wound dressing barrier is illustrated.

With reference to FIGS. 1A-1D, a vented wound dressing barrier 100 is illustrated with a plurality of vents 20 arranged in a pattern on a membrane layer 10. As illustrated, the vented wound dressing barrier 100 may include one or more membrane layers 10 stacked together to form a laminate. As understood, the membrane layer 10 forms part of the vented wound dressing barrier 100. As shown, cuts are made in the surface area through the one or more membrane layers 10. These cuts define a perimeter of a vent 20. As shown in FIGS. 1A-1D, the perimeter is basically a "U" shape having an arcuate or a rounded end somewhat elliptical in configuration that stops at a location such that a portion of the vent 20 is left integral to the membrane layer 10 in such a way as to form a hinge. The vents 20 having been cut using a die 500 as shown in FIGS. 10A and 10B that creates these cut lines along the perimeter such that no material is removed during the process of die cutting the vents 20 into the membrane layer 10 across the surface area as indicated. As such, in normal use the vents 20 are in a closed configuration such that there is a cut line for each vent 20 that allows the vent 20 to move either inwardly or outwardly as a result of any inward or outward forces applied. This is particularly useful in the area of wound dressings in that should there be fluid underlying a bandage or dressing barrier, the fluid can be drained allowing the fluid to seep past the wound dressing barrier 100 through the vents 20 in the one or more membrane layers 10.

Figure 1B:
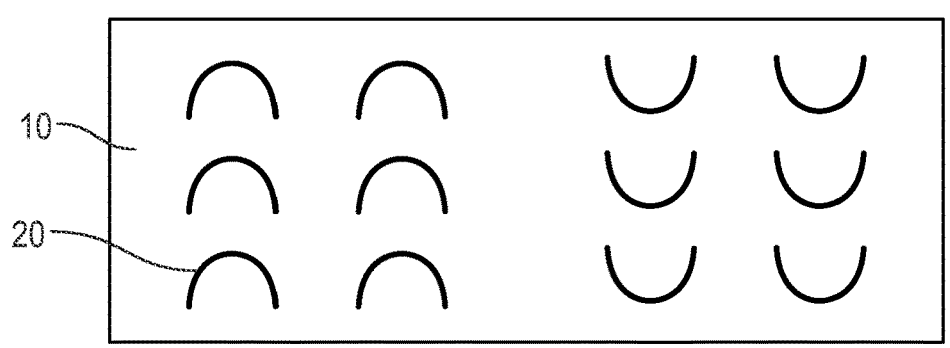
FIG. 1B is a perspective view of an exemplary vented wound dressing barrier similar to FIG. 1A with arcuate cut vent openings in a different orientation configuration.
Figure 1C:
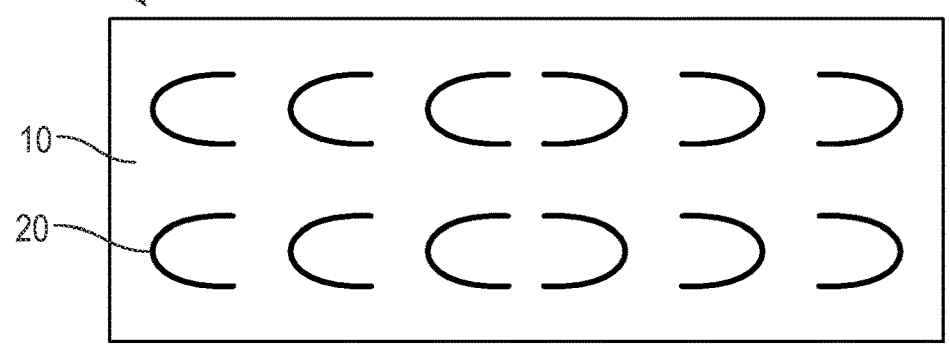
FIG. 1C is a perspective view of an exemplary vented wound dressing barrier similar to FIG. 1A with arcuate cut vent openings in a different orientation configuration.
Figure 1D:
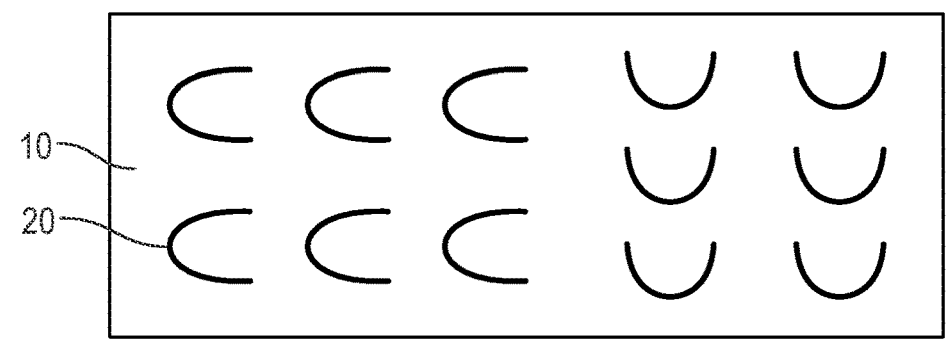
FIG. 1D is a perspective view of an exemplary vented wound dressing barrier similar to FIG. 1A with arcuate cut vent openings in a different orientation configuration.

As shown in FIG. 1A, the vents 20 are aligned in two parallel rows extending across the surface area of the membrane layer 10. In FIG. 1B, the vents 20 are shown with half of the vents 20 extending across the width in two rows with the hinge portion of the vent 20 at a lower section relative to the right-hand side of the membrane layer 10 where the vents 20 are shown oppositely oriented with the hinge upper portion of the membrane layer 10. Similarly in FIG. 1C, the vents 20 are shown in two rows as in FIG. 1A, but in this case in one row half are pointed in one direction and the other half in an opposite direction from the midline of the membrane layer 10. In FIG. 1D, the vents 20 are shown oriented in a horizontally extending two rows on half the membrane layer 10 and in a vertical two rows on the opposite half of the membrane layer 10. In any fashion, these arrangements of the vents 20 can be oriented in any pattern that one chooses for the particular wound dressing barrier 100 application.

Figure 2A:
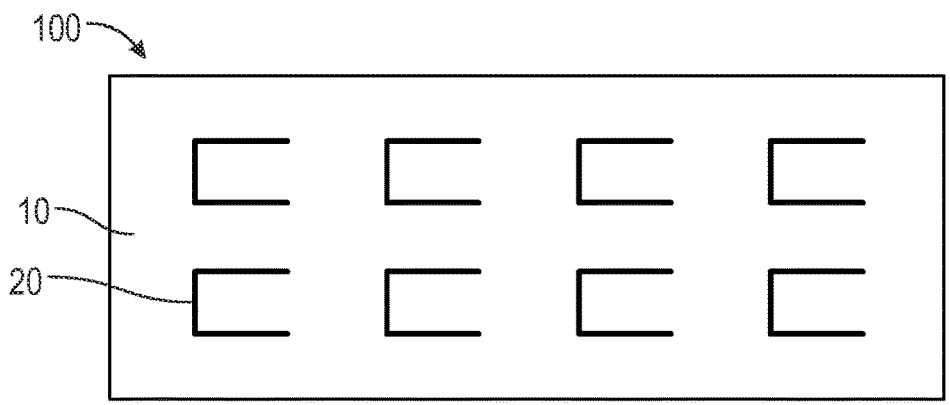
FIG. 2A is a perspective view of an exemplary vented wound dressing barrier of the present invention in a square or rectangular shape with a plurality of 3-sided square or rectangular cut vent openings.
Figure 2B:
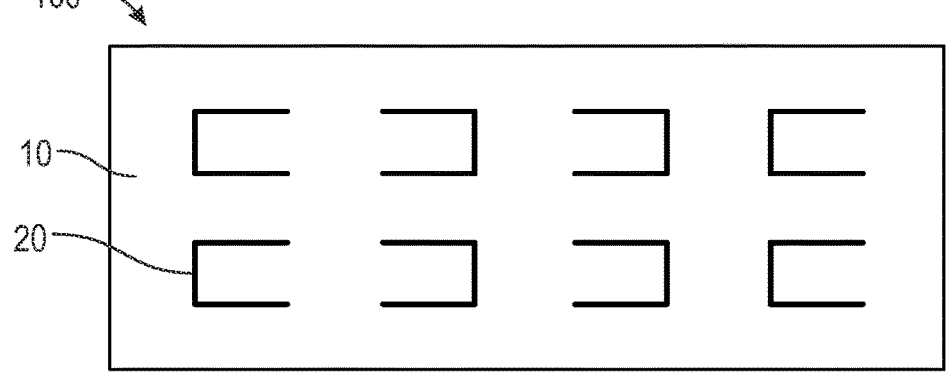
FIG. 2B is a perspective view of an exemplary vented wound dressing barrier similar to FIG. 2A with 3-sided square or rectangular cut vent openings in a different orientation configuration.
Figure 2C:
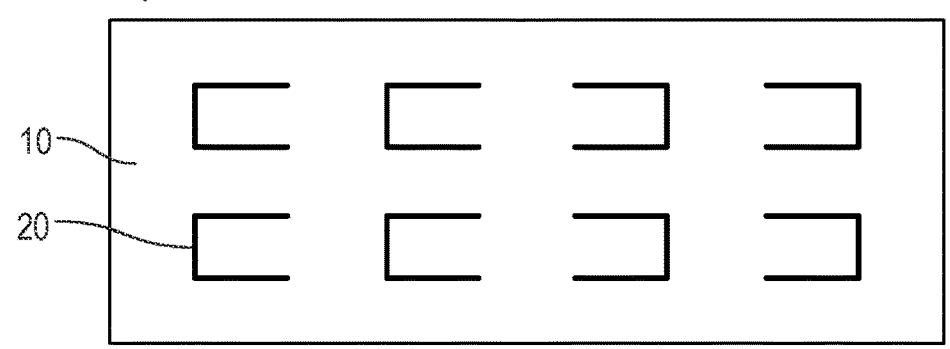
FIG. 2C is a perspective view of an exemplary vented wound dressing barrier similar to FIG. 2A with 3-sided square or rectangular cut vent openings in a different orientation configuration.
Figure 2D:
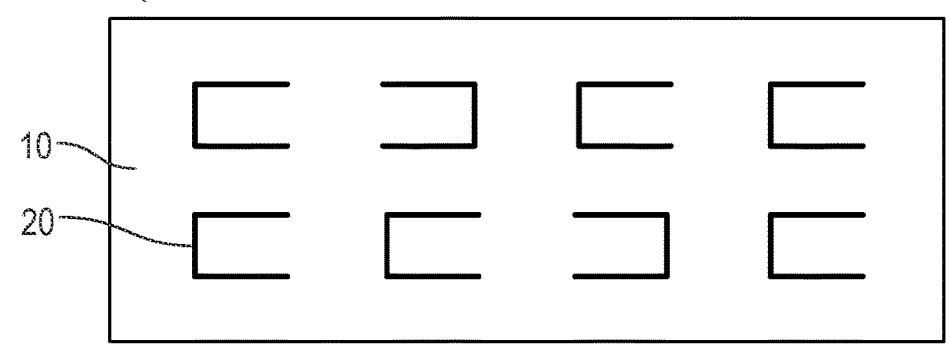
FIG. 2D is a perspective view of an exemplary vented wound dressing barrier similar to FIG. 2A with 3-sided square or rectangular cut vent openings in a different orientation configuration.

With reference to FIGS. 2A-2D another embodiment of the invention is shown wherein the vents 20 are made in a rectangular shape with one side along the vent 20 perimeter such that one portion of the vent 20 remains integrally attached to the membrane layer 10 as previously discussed. In these embodiments shown in FIGS. 2A-2D, all of the vents 20 have the rectangular or square shape with the hinge location representing the part of the perimeter that is not cut. As illustrated in FIG. 2A, all of the vents 20 are oriented in a similar direction with the hinged end of the vent on the right-hand side of the membrane layer 10. As shown in FIG. 2B, the vents 20 are shown in two rows wherein the adjacent vents 20 are hinged on the left-hand side in one orientation and oppositely oriented on the right-hand side as illustrated. In this case on the left-hand side the vents 20 have the hinge locations in closer proximity to each other whereas on the right-hand side the vents are extended further away from each other on that portion of the membrane layer 10. In FIG. 2C, the vents 20 are shown in two rows with the vents 20 on the left-hand side having the hinged location in one direction and the vents 20 on the right-hand side having the hinged location in the opposite direction such that when the vents 20 open they open relative to the hinge in opposite directions on each half of the membrane layer 10. FIG. 2D has the vents 20 oriented such the top half is shown with the left hand side of the membrane layer 10 having the vents 20 in an opposite configuration with the hinged location in close proximity on the top row but the bottom row shows the vents 20 oriented with the hinged locations in a different orientation relative to each other such that the top row and bottom row match on the extreme left whereas the next adjacent vents 20 in the top row and bottom row are oriented in opposite directions as is true on the right hand side where the upper vents 20 and lower vents 20 are oriented opposite directions whereas the far right side the vents 20 are oriented in the same direction.

Figure 3A:
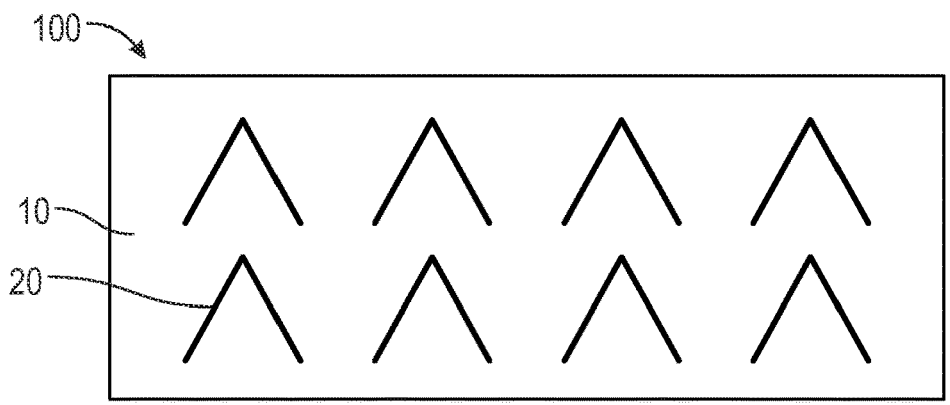
FIG. 3A is a perspective view of an exemplary vented wound dressing barrier of the present invention in a square or rectangular shape with a plurality of 3-sided square or rectangular cut vent openings.
Figure 3B:
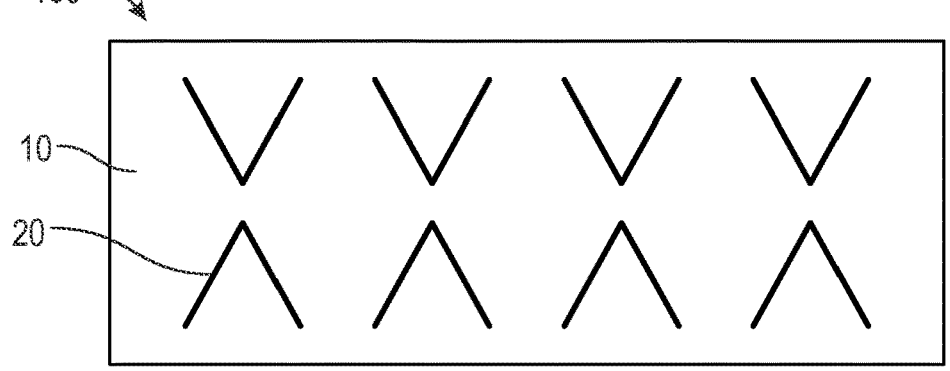
FIG. 3B is a perspective view of an exemplary vented wound dressing barrier similar to FIG. 3A with triangular cut vent openings in a different orientation configuration.
Figure 3C:
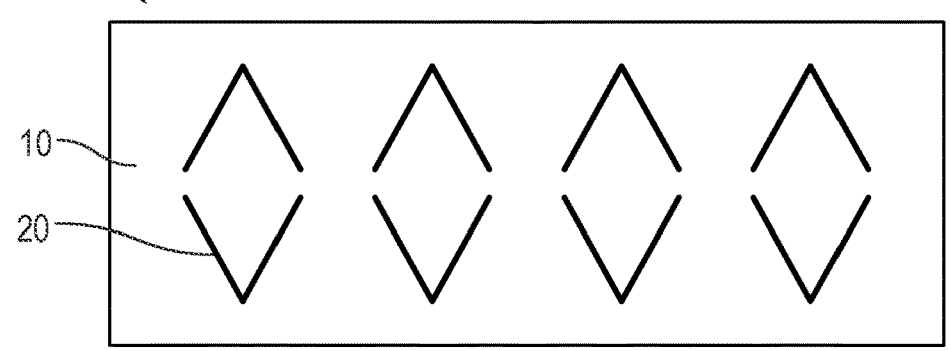
FIG. 3C is a perspective view of an exemplary vented wound dressing barrier similar to FIG. 3A with triangular cut vent openings in a different orientation configuration.
Figure 3D:
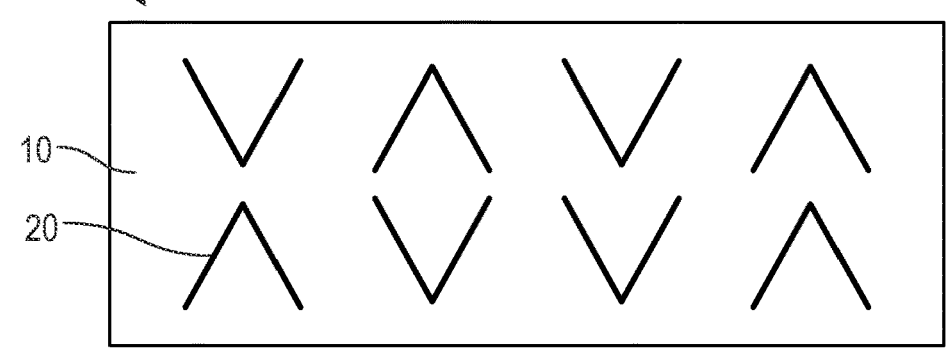
FIG. 3D is a perspective view of an exemplary vented wound dressing barrier similar to FIG. 3A with triangular cut vent openings in a different orientation configuration.

In FIGS. 3A-3D the vents 20 are created by a triangular shape with the cut lines along the perimeter are exhibited by two lines extending from an apex or point down inwardly to a hinged portion of the perimeter. As shown in FIG. 3A all of the triangular vents 20 are positioned in such a fashion that the apexes are pointed to an upper side of the membrane layer 10 to one side of the membrane layer 10. In FIG. 3B, the apexes are pointing towards each other relative to the upper and lower row of vents 20. As such the hinged locations are along the outer perimeter of the membrane layer 10 in that the vents 20 will open from the center line outward to allow for fluid flow drainage from the wound. In FIG. 3C, the hinge locations of the various triangle shaped vents 20 are shown aligned relative to each other such that the apexes extend towards each side, the top row extending toward a top side of the membrane layer 10 and the lower row extending to a bottom side of the membrane layer 10. As such, when the vents 20, they open oppositely relative to each other. In FIG. 3D, there is an assortment of the triangular shaped vents 20 such that the vents are oriented with the apexes one up, one down across the rows in such a fashion that they are the opposite on the top row and bottom row on the left-hand side and on the right-hand side they are identical in terms of the hinge location. These provide various alternative ways of providing drainage using the triangular vents 20.

Figure 4A:
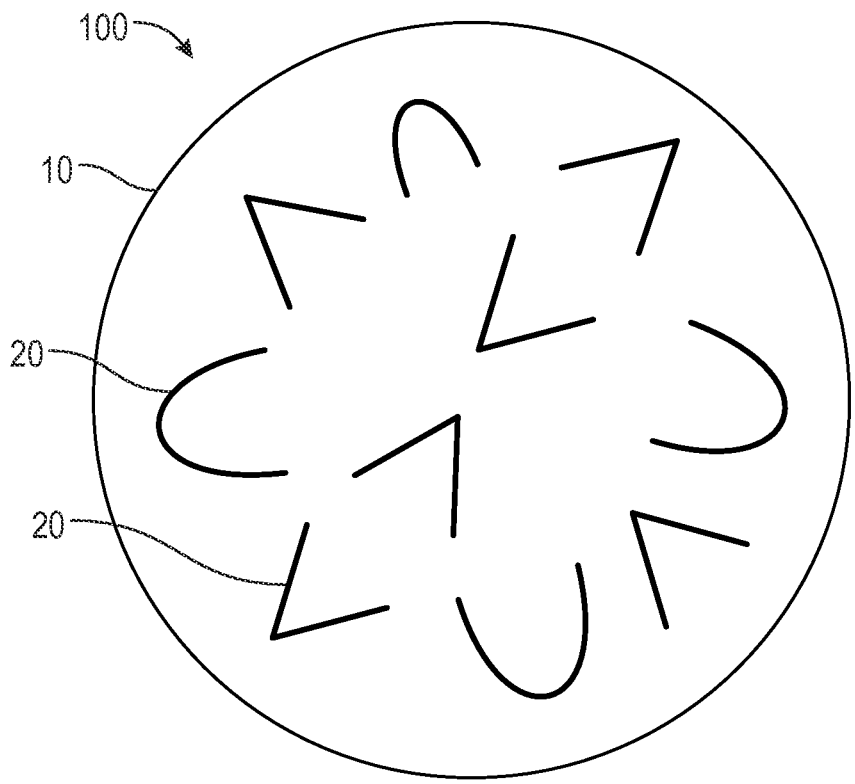
FIG. 4A is a perspective view of an exemplary vented wound dressing barrier of the present invention in a circular shape with a combination of arcuate and triangular cut vent openings.
Figure 4B:
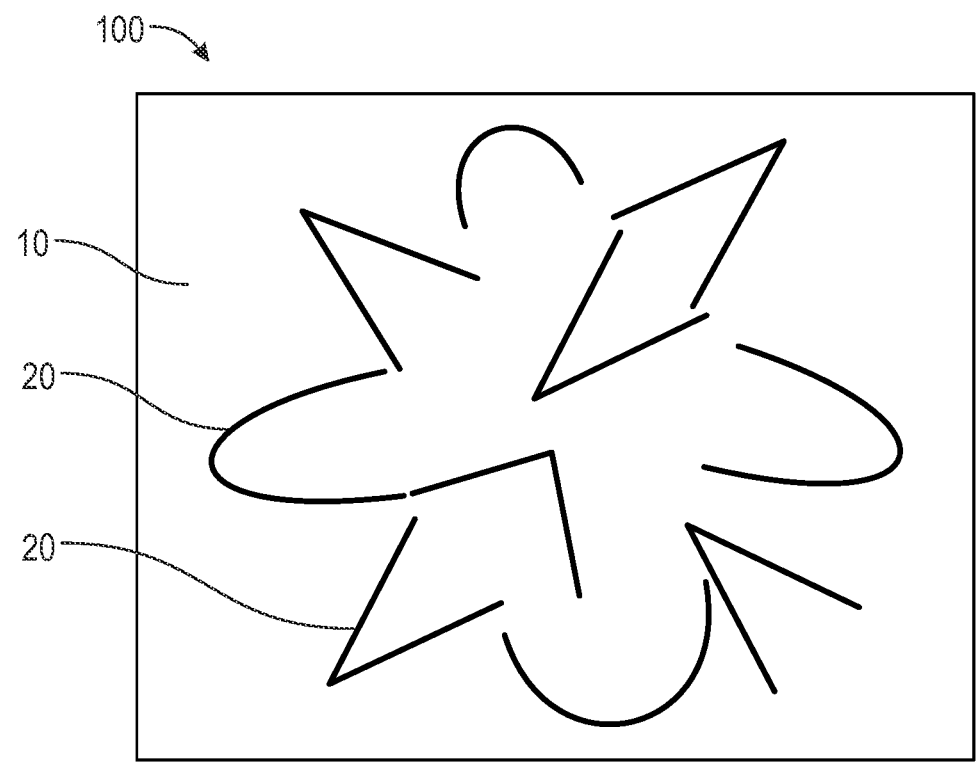
FIG. 4B is a perspective view of an exemplary vented wound dressing barrier in a square or rectangular shape with a combination of arcuate and triangular cut vent openings similar to FIG. 4A.

With reference to FIGS. 4A and 4B, FIG. 4A the membrane layer 10 is shown as a circular membrane layer onto which a variety of vents 20 are illustrated. As shown, the combination of vents 20 oriented around the circular perimeter of the membrane layer 10 with a row of triangular vents 20 extending across one side as illustrated. The hinged locations are provided in these embodiments as shown. With reference to FIG. 4B, a square membrane layer 10 is illustrated with a plurality of vents 20 wherein some cases the vents 20 are somewhat aligned in close proximity such that a common hinge location is located on some of these vents 20. This figure shows a more random nature of orienting the vents 20 so that a maximum amount of fluid drainage can be achieved in these configurations.

Figure 5:
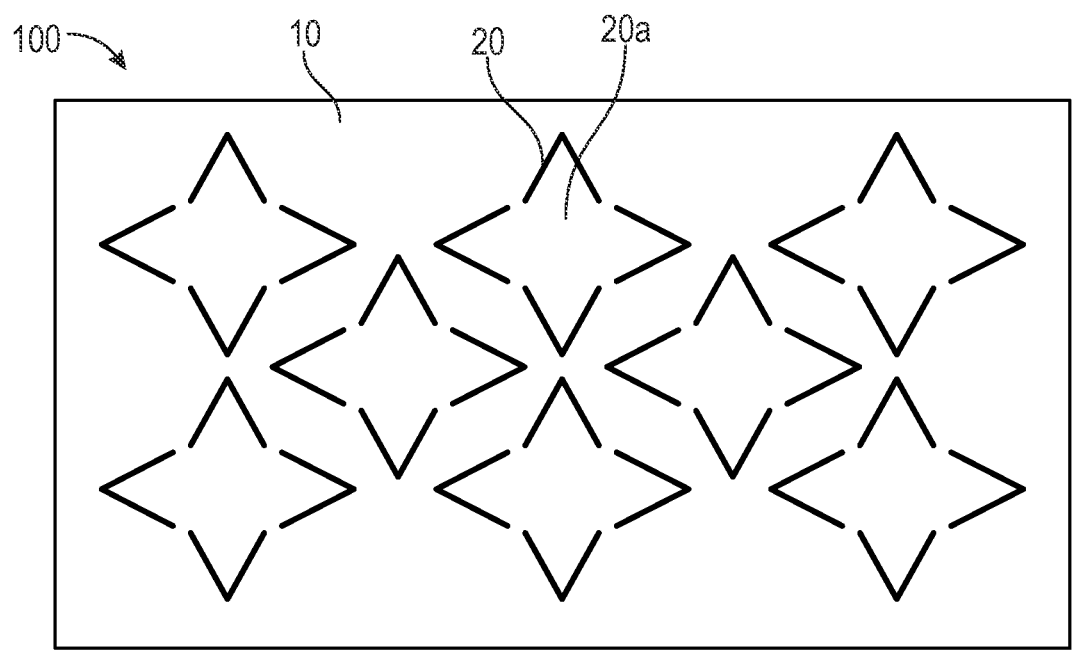
FIG. 5 is a perspective view of an exemplary vented wound dressing barrier of the present invention in a square or rectangular shape with a plurality of triangular cut vent openings arranged in groups of 4 vent openings.

With reference to FIG. 5, a rectangular membrane layer 10 is shown wherein a plurality of vents 20 are oriented in a somewhat star like configuration or pattern 20a such that the hinge locations are inward of these vents 20. As shown, each star pattern 20a comprises four triangular vents 20 arranged around a surface area of the membrane layer 10 as illustrated. Each of the vents 20 is oriented such that it can open as similarly described earlier.

Figure 6A:
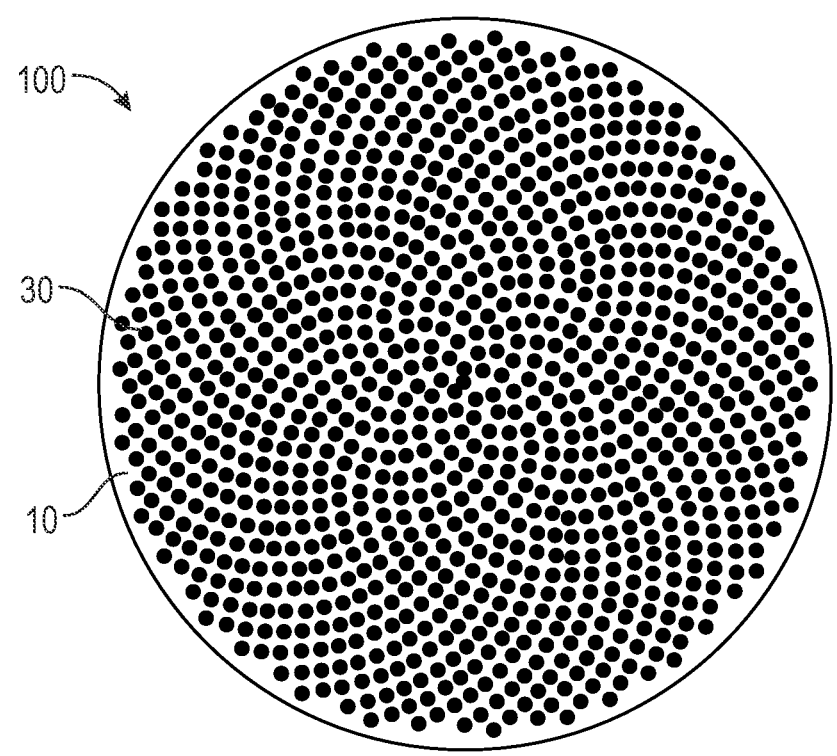
FIG. 6A is a perspective view of an exemplary vented wound dressing barrier of the present invention in a circular shape with a random, variable density, infinitely random Fibonacci cut vent openings.
Figure 6B:
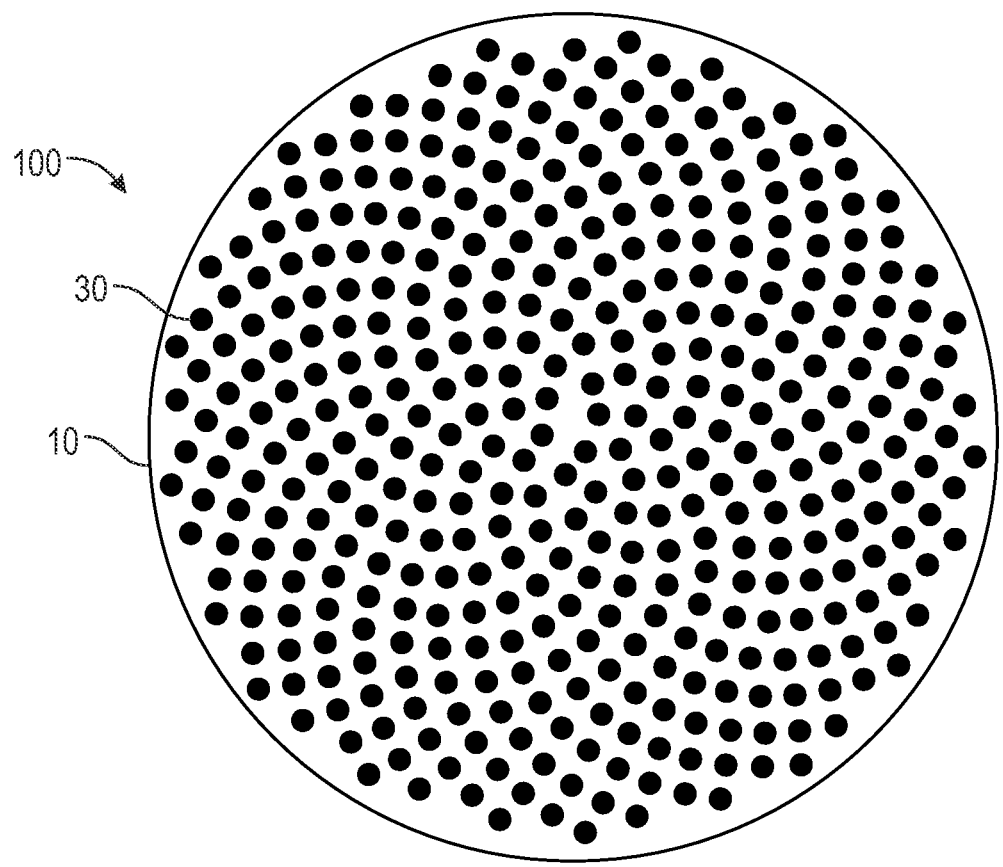
FIG. 6B is a perspective view of an exemplary vented wound dressing barrier in a circular shape with a random, variable density, infinitely random Fibonacci cut vent openings similar to FIG. 6A.

With reference to FIG. 6A, a membrane layer 10 is illustrated having a plurality of perforations or holes 30. These perforations 30 are shown as black dots on the circular membrane layer 10. The black dots are arranged in a Fibonacci pattern in FIGS. 6A and 6B. FIG. 6B is similar to FIG. 6A other than the pattern is larger with hole 30 diameters larger. FIGS. 6A and 6B are shown to indicate that certain of combinations of perforations 30 and vents 20 can be employed in the wound dressing barrier 100.

Figure 7A:
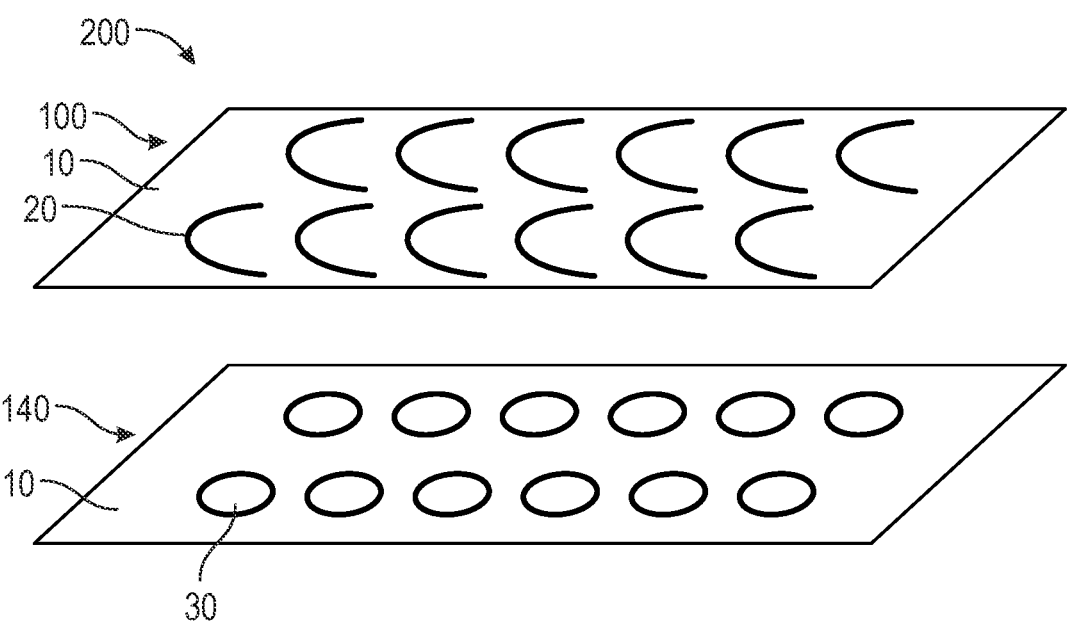
FIG. 7A is an exploded view of an exemplary two-layer vented wound dressing barrier of the present invention in a square or rectangular shape showing a first layer vented wound dressing barrier with a plurality of arcuate cut vent openings above a second layer vented wound dressing barrier with circular openings or perforations.
Figure 7B:
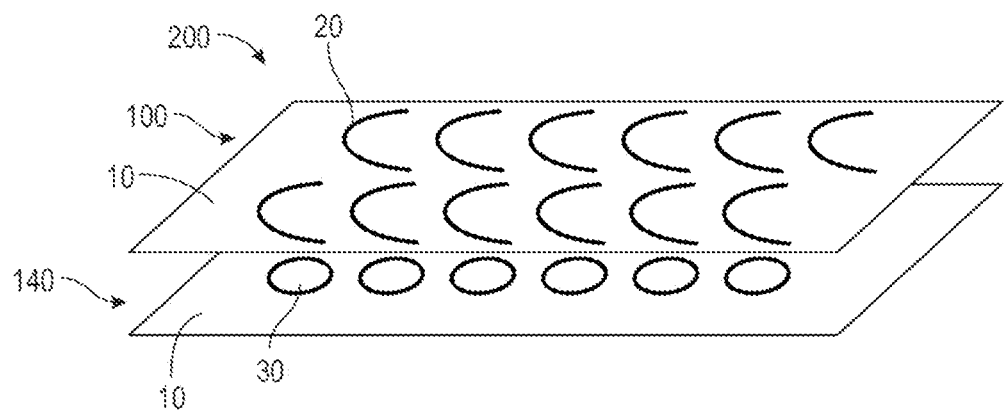
FIG. 7B is a similar exploded view of FIG. 7A showing the two layers in a closer configuration.

In FIG. 7A another embodiment is illustrated wherein the wound dressing barrier 100 with membrane layer 10 and vents 20 taken from FIG. 1A is illustrated layered on top as an exploded view over a base layer 140 with a membrane layer 10 having perforations or holes 30 to form a laminated wound dressing barrier 200. In this configuration, it is important to note that the holes 30 are in an underlying base layer 140 such that the wound dressing barrier 200 would have the perforated base layer 140 lying against the wound area and the vented wound dressing barrier 100 stacked or laminated above the perforations 30 in a stack of layers to form the wound dressing barrier 200. In use, these layers will be stacked together in such a fashion that as fluid passes through the openings or holes 30 of the perforations, they would contact the vent area because the holes 30 are aligned with the vent area 20 when assembled in such a fashion that the vents 20 can open freely to any internal pressure. FIG. 7B shows the two layers of wound dressing barriers 100, 140 in closer proximity. In practice, these layers 100, 140 would be laminated together forming the laminated wound dressing barrier 200.

Figure 7C:
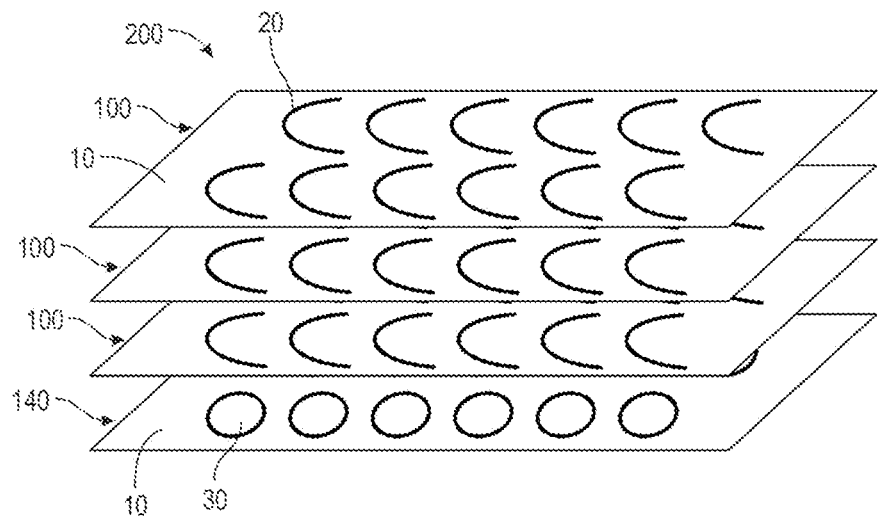
FIG. 7C is a view of a four-layer vented wound dressing barrier consisting of two sets of the two-layer vented wound dressing barrier of FIGS. 7A and 7B.

In FIG. 7C, multiple wound dressing barriers 100 with vents 20 are shown stacked above each other, all above a base layer 140 with perforations 30 to form the laminated wound dressing barrier 200. In this embodiment, a multi-layer membrane stack with vents 20 is employed over a base layer 140 with perforations 30. Again, since all the vents 20 are aligned the vents 20 can open together when laminated without any impedance from the perforations or holes 30. The advantage of using perforations or holes 30 in an underlying base layer 140 is that if the holes 30 are of a smaller diameter than the vent 20 perimeter, the underlying base layer 140 will form a lip such that the vents 20 above cannot push downward through the holes 30 and will be restricted from an inward opening movement of the vents 20. This prevents the vents 20 from extending inwardly and keeps the vents 20 in alignment with the membrane layers 10 until internal pressures or fluids are created that would cause the vents 20 to open outwardly relative to the membrane layer 10 structure. This is believed beneficial, and by using a combination of layers enhances the strength of the individual membranes 10 because it creates a stacked or laminated wound barrier 200 construction.

Figure 7D:
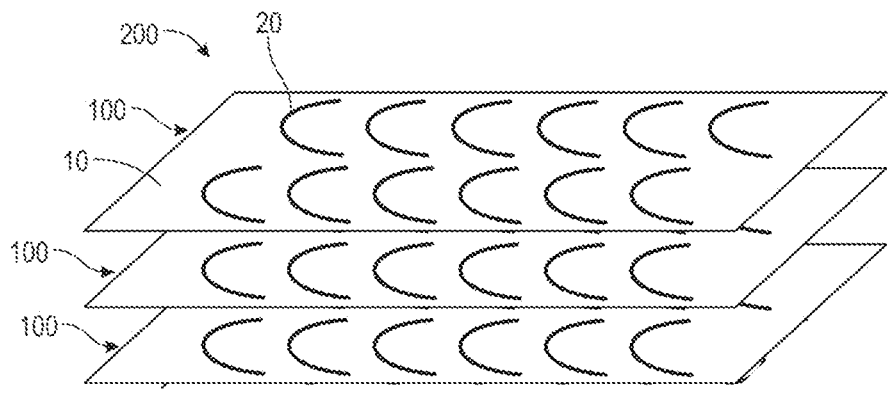
FIG. 7D is a view of a three-layer vented wound dressing barrier.

With reference to FIG. 7D, a multi-layer wound dressing barrier 200 is shown. This alternative embodiment shows a plurality of single layer wound dressing barriers 100 with membrane layers 10 stacked or laminated together to form the laminated membrane dressing barrier 200 with the vents 20 aligned for fluid drainage similar to FIG. 7C but without the perforated base layer 140.

Figure 8:
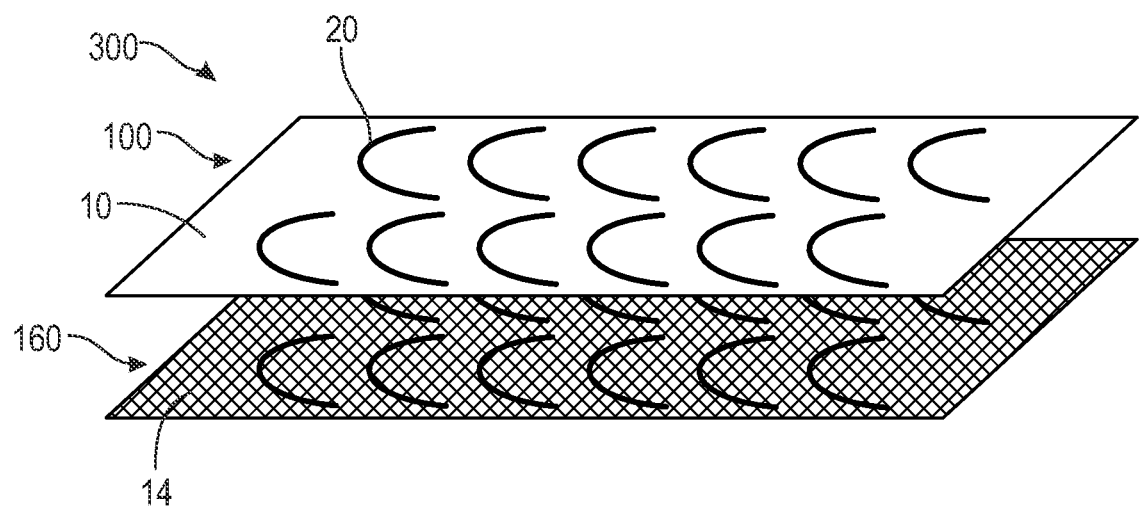
FIG. 8 is a view of a two-layer vented wound dressing barrier consisting of a vented membrane layer and a vented synthetic or fabric layer.

With reference to FIG. 8 another embodiment is shown wherein a laminated wound dressing barrier 300 has a bottom base layer 160 that could be a synthetic or polymer, or net or gauze or other material such that the top vented wound dressing barrier 100 lies on top of the bottom base layer 160 and the vents 20 of all layers are free to open. In this embodiment, the laminated wound dressing barrier 300 has one or more synthetic or electrospun fabric layers 14 attached to the one or more membrane layers 10. The one or more synthetic or electrospun fabric layers 14 having a plurality of vents 20 aligned with the vents 20 of the one or more membrane layers 10 configured to open with the vents 20 of the one or more membrane layers 10 to allow drainage of fluids from a wound.

Figure 9:
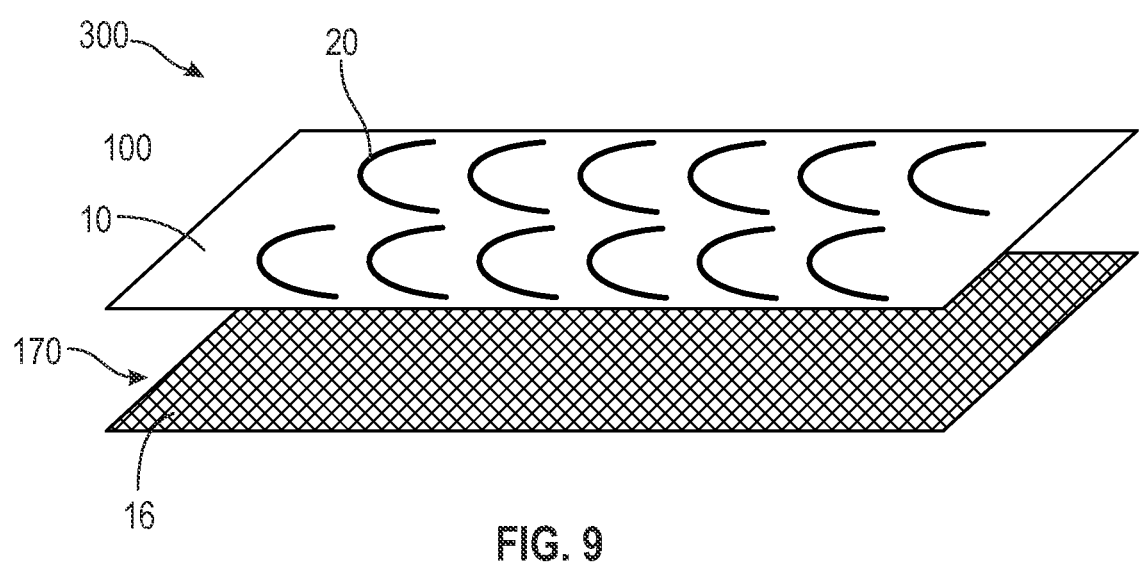
FIG. 9 is a view of a two-layer vented wound dressing barrier consisting of a vented membrane layer and a non-vented synthetic or fabric base layer.
Figure 10A:
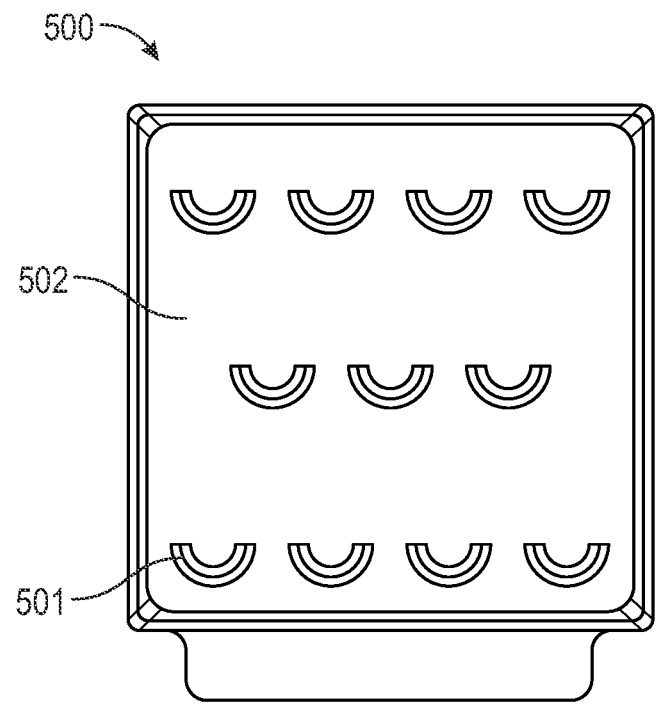
FIG. 10A is a schematic view of an exemplary die tool for forming the vented openings in the vented wound dressing barriers of the present invention.
Figure 10B:
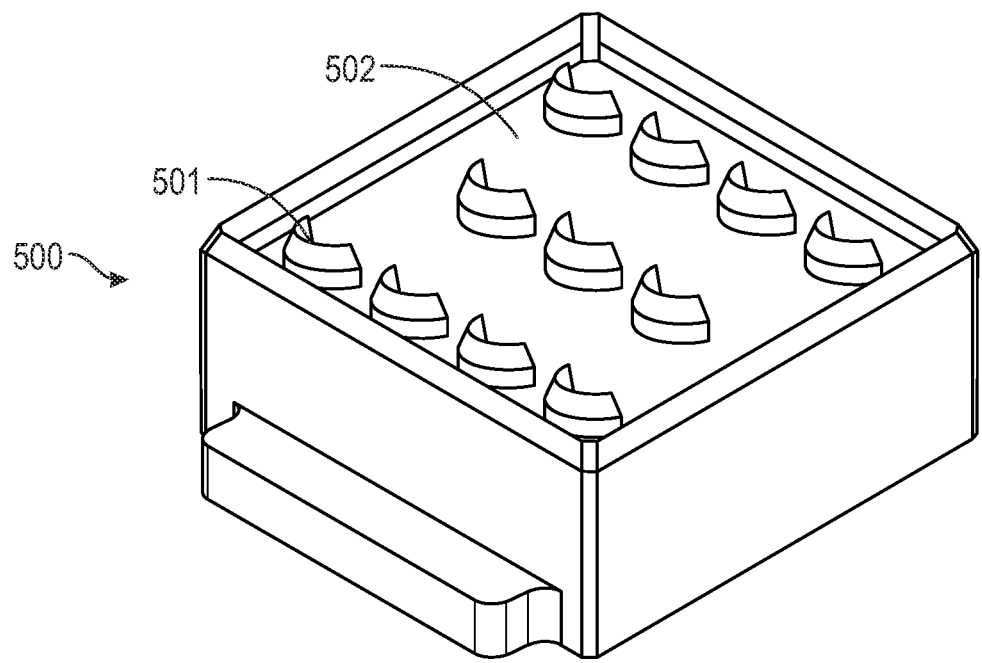
FIG. 10B is a perspective view of the exemplary die tool taken from FIG. 10A.

FIG. 9 shows another embodiment where an underlying base layer 170 is a gauze or mesh or other type material layer 16 that is a completely open net like structure which could be made from any biocompatible material such that it could be easily absorbed by the tissue during wound healing. However, it allows for the one or more vented wound dressing barriers 100 to be laminated or stacked on top of the base layer 170 in order to achieve the necessary drainage as previously discussed while also restricting the movement of the vents 20 from opening inwardly relative to the base layer 170.

With reference to FIGS. 10A and 10B, a die tool 500 is illustrated. A top view of the die tool 500 is shown in FIG. 10A showing the ability to cut one of the exemplary vents. This is illustrated in a perspective view in FIG. 10B. In this configuration, a square membrane layer 10 would be used and when the membrane layer 10 is pressed against the protrusions 501 to the die surface 502 of the cutting die 500 would create the cut edges of the vents.

The vented wound dressing barrier further can have one or more combinations of chitosan, polymer-based, collagen dressings, hydrocolloids, hydrogels, fibers, gauze, alginates, foams, matrix elaborations including hyaluronic acid, cell-matrix combinations, matrix-exosome combinations, matrix-secretome combinations, infusions, perfusions, and other topical wound dressings intended to cover surface wounds of varying depths.

In another embodiment, the vented wound dressing barrier is cryoprotected, bioprotected, freeze-dried, air-puffed, thermally imbued with at-melting point modification, embossed, channeled, or in other ways have topographical modifications inherent to individual lamina or in register combine to create hollowed or microfluidic conduits between layers. In one of the preferred embodiments, at least one of the one or more membrane layers 10 is a placental tissue membrane. The one or more membrane layers 10 with a plurality of vents can be multiple membrane layers of amnion or chorion or combinations of amnion and chorion layers stacked to form a multi-layered laminate membrane wound dressing barrier 200, 300. The plurality of vents are oriented and arranged in patterns or are oriented in random orientations. The plurality of vents can be made in random sizes or shapes in the one or more membrane layers. The random shapes can be one or more of a crescent, rhomboid, triangular, round or elliptical shape.

In one embodiment, the vented wound dressing barrier further has a cryoprotectant coating. The cryoprotectant coating covering the one or more membrane layers 10 and wherein the combination of the one or more membrane layers with the cryoprotectant coating are dried or freeze-dried to form a dried or freeze-dried coated vented wound dressing barrier.

The cryoprotectant is preferably a polyampholyte tissue protectant and is non-toxic. The coating provides a reduction in inflammation at the would site and enhances healing of the wound.

As mentioned above, the vented wound dressing barrier 100, 200, 300 can be coated by immersing the membrane layers 10 in a cryoprotectant, preferably a polyampholyte cryoprotectant that is non-toxic and wherein the residual coating can be left on the membrane layers at the time of use without requiring washing or rinsing to remove the coating. In fact, the coating has been found to reduce inflammation at the wound site and enhance the healing process.

As discussed, this unique cryopreservation liquid according to the invention is obtained by dissolving a polymer such as poly-lysine in physiological solutions by 1-50 w/w %; preferably by 2-20 w/w %, particularly preferably by 3-15 w/w %, and more preferably by 5-10 w/w %. The physiological solutions to be used are a physiological saline as well as culture media for culturing various cells and tissues. For example, Dulbecco-modified eagle MEM culture medium (DMEM) may be one of the preferable culture media. In place of, or in addition to poly-lysine, polyallylamines may be used. In place of these, or in addition to at least one of these, a compound(s) to be used is/are selected from other polyamines such as amino-group-introduced polysaccharides, and poly-amino acids such as poly-arginine, poly-glutamic acid and poly-aspartic acid; also a polysaccharide compound(s) that is/are selected from dextran, dextrin, pullulan and chitosan as well as polycarboxylic acid such as polyacrylic acid.

Among these polymers, preferable are polymers having a structure obtainable by polymerization of a monomer compound(s) that have both cationic and anionic substituent groups within the same monomer molecules; and especially preferable is poly-amino acids. In other words, especially preferable is a polymer having a repeating unit that has both amino and carboxyl groups. Poly-lysine to be used can be either ε-poly-L-lysine or ε-poly-D-lysine or a-poly-L-lysine. Cryoprotectant polymers have molecular weights between 100 and 100,000. The most preferable polymers fall into a group of ε-poly-L-lysine routinely used as food additives. These are either synthesized by enzymes or produced by the *Streptomyces* fungi and have the average molecular weights of 1000-20,000, and particularly those of 1000-10,000 with polymerization degrees ranging between 15-35, and those with 20 or lower are attempted to be produced. The average molecular weights or the average polymerization degrees are easily measurable by sodium dodecyl sulfate-polyacrylamide gel electrophoresis (SDS-PAGE), by using an electrophoresis apparatus as a means of evaluating density. Standard protein markers are used for the measurement. The poly-lysine may be heat-treated to increase its molecular weights greater than 30,000 and used as the polymer compound. However, the molecular weight range mentioned above is preferable due to the increasing viscosity with molecular weight. Because the poly-lysine having a free terminal carboxyl group has side-chain primary amino groups, their partial amidation by dicarboxylic anhydrides greatly gives excellent miscibility and solubilization performance described later. Other particularly favorable polymer compounds also adoptable according to the invention are polyallylamines with average molecular weights of 1000-1,000,000, preferably 1000-20,000. For examples, such adoptable polymers are: aqueous solution of the allylamine polymer (PAA-03 of Nitto Boseki Co., Ltd.) added with acetic anhydride or acetic acid; and the partially-methoxy-carbonylated allylamine polymer (PAA-U5000 of Nitto Boseki Co., Ltd.). The allylamine polymer, in same manner with the poly-lysine, has as side-chain groups primary amino groups only, but density of the primary amino group per unit molecular weight is larger in the allylamine polymer than in the poly-lysine. And, when the allylamine is partially carboxylated, obtained polymer compound is considered to act in same manner with partially-carboxylated poly-lysine mentioned later.

Preferably, the amino groups of the polyamine are partially blocked by being carboxylated or acetylated with carboxylic acid anhydride(s). This blockage is done by the carboxylation or acetylation of the amino groups to the degrees of preferably 50-99 mol %, particularly 50-93 mol %, more preferably 50-90 mol %, still more preferably 55-80 mol %, and the most preferably 58-76 mol %. About 50% of the amino group would be blocked by being reacted with 52-53 mol % of anhydrous carboxylic acid on basis of molar amount of the amino groups in the polyamine. In a normal reaction condition, 90-95% of the amino groups would be blocked when reacted with 100 mol % anhydrous carboxylic acid. The blocking rates above or below the above-mentioned ranges would decrease cryopreservation effects. Carboxylic acid anhydrides adoptable herein include acetic anhydride, citric anhydride, succinic anhydride, glutaric anhydride, malic anhydride, fumaric anhydride and maleic anhydride. Among these, succinic anhydride and acetic anhydride are particularly preferred.

However, polyamine with amino groups not blocked as free may also be used; thus adoptable are the degrees of carboxylation and acetylation throughout a range of 0-100 mol/mol %. In the present invention, polycarboxylic acid in which a part of the carboxyl groups is aminated may be used. More specifically, polycarboxylic acid may be partially aminated by reacting its carboxyl group with compounds such as diamine, triamine and the polyamine. Adoptable diamines are ethylenediamine and hydrazides such as adipodihydrazide. Reaction of these amino compounds with carboxylic acid is by way of addition reaction with carbodiimide. In such occasion, adoptable is the degree of amination in a range of 0-100 mol/mol %. In same manner with blockage of amino groups, percentage of remaining carboxyl groups is preferably in a range of 50-99 mol %, more preferably in a range of 60-97 mol %, in each of which remaining percentage is for aminated carboxylic groups. For example, polyacrylic acid having average molecular weights of 1000-3,000,000, or 1000-10,000 in particular, is used; and 1-50 mol % of, preferably 3-40 mol % of, carboxyl groups of the polyacrylic acid are blocked with amines and carbodiimides such as ethylenediamine dihydrazide, or the like. Cryopreservation liquid according to the invention may also contain 0.3-15 w/w %, or 0.1-50 w/w % in particular, of conventional cryoprotectant materials such as DMSO, glycerol, ethylene glycol, trehalose or sucrose. Because cells are subject to damages caused by the oxidation stress during freezing and thawing, the addition of anti-oxidants to the cryoprotectant is expected to improve its preserving effects. For examples, anti-oxidants such as catalase, peroxidase, superoxide dismutase, vitamin E, vitamin C, polyphenols such as epigallocatechin gallate or glutathione may be used.

The osmotic pressure of the cryopreservation agent according to the invention is 200-1000 mOsm/kg, more preferably is 300-700 mOsm/kg, and further preferably 400-600 mOsm/kg. The cryopreservation agent according to the invention is applicable to the preservation of not only cells but also tissues. Examples of such cells and tissues to be cryopreserved by the cryopreservation agent are cultured cell lines, fertilized eggs of animal and human origin. Further examples are sperm cells, embryonic stem cells, IFS cells, mesenchymal stem cells, haemopoietic stem cells, neuronal stem cells, umbilical cord blood stem cells, hepatocytes, nerve cells, cardiomyocytes, vascular endothelial cells, vascular smooth muscle cells and blood cells. Not only animal or human cells but also plant cells can be included. Tissues and organs that are able to be preserved by the cryopreservation agent according to this invention are skins, nerves, blood vessels, cartilages, cornea, livers, kidneys, hearts and pancreatic islets.

Additional novelty of this invention is afforded in the variation in osmolality invigorated during the sublimation process. The loss of water suspends the materials in a static and transient state of relative harmony. With rehydration in the use of the product in saline, or in patient care, or in common practice of combination with other allografts, differences extant to the original formulation are extended to new metabolic demands. Variations in shape and thickness and absorption will define the destiny of whole, fragment, coated, fractured, and cellular organelles.

An interesting aspect of the present invention is the ability to adjust the pH from the preferred range of 7.4 to greater or lesser amounts. This allows the electro field charge to be adjusted greater or lower as a tailored means of increasing or decreasing the predetermined time for the coating to be metabolized. Alternatively, the mixture and the protectant can be diluted prior to implantation with sterile water or saline or host blood to thin the protectant coating to shorten the time to be metabolized if so desired. In any event, the present invention insures no rinsing or separation of the protectant from the cells is required insuring much higher survivability of the donor mixture.

Membrane venting allows for fluid drainage. The invention creates hinged flaps, chads and allows for exudate drainage during the healing process. The goal is to improve healing response for high exudate wounds and prevent impedance of fluid drainage without reducing coverage, which can present as pressure increases as noted in compartment syndromes. This provides the benefit of laminations that do not suppress perforation and fluid exchange and contain an upper lamination that has a hinged surface that can open to prevent pressure edema. Enhanced bio-protection is achieved during cryoprotection using VIA Coat, a cryoprotectant, or a polyampholyte tissue protectant as a coating that, along with the vented wound dressing barrier is dried or freeze-dried for convenient room temperature storage prior to use.

This vented wound dressing barrier retains key dressing properties, remains sterile, non-cytotoxic, non-allergenic and protects the wound from bacteria and foreign material. It absorbs exudate from wounds, prevents heat and excessive fluid loss from wounds, provides compression to minimize edema and obliterate dead space and can be made non-adherent to limit wound disruption. It creates and sustains a warm, moist environment to maximize epithelialization, minimizes pain and is flexible and conforms to any contour.

The laminate stacks when combining a sublaminar perforation base layer yield superior venting allowing draining with a check valve function. Applications of this wound dressing barrier are compatible with and enhance wound vacuum treatments.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. The surgical access window described herein encompasses the dimensions presented and any and all variations applicable to the methods and surgical technique described directly or indirectly intended with this device.

What is claimed is:

1. A vented wound dressing barrier comprising:
a vented wound dressing barrier, the vented wound dressing barrier including one or more membrane layers with a plurality of vents, the vents being cut along a perimeter of the vents through the one or more membrane layers and having a connection portion uncut relative to the one or more membrane layers thereby forming a hinge configured to allow the vents to open for drainage when exposed to fluid underlying the vented wound dressing barrier, wherein the vented wound dressing barrier further comprises a base layer underlying and attached to an inner surface of one of the one or more membrane layers, the base layer having a plurality of holes, the plurality of holes being aligned with the plurality of vents and wherein the holes of the base layer are sized smaller than the cut perimeter of the vents.

2. The vented wound dressing barrier of claim 1 wherein at least one of the one or more membrane layers is a placental tissue membrane.

3. The vented wound dressing barrier of claim 1 wherein the plurality of vents are each cut along the perimeter without removal of any of the membrane layer.

4. The vented wound dressing barrier of claim 1 wherein the plurality of vents in each of the one or more membrane layers are at least partially aligned.

5. The vented wound dressing barrier of claim 3 wherein the one or more membrane layers with the plurality of vents has a surface area for covering a wound, the surface area in the absence of a fluid pressing on the vents having no openings or voids which reduce a vented wound dressing barrier area covering a wound.

6. The vented wound dressing barrier of claim 1 wherein the holes of the base layer are aligned at least partially with the cut perimeter of the vents to reduce the flow through the vents.

7. The vented wound dressing barrier of claim 1 wherein the vents of the one or more membrane layers overlay the holes of the base layer and the base layer forms a lip preventing the vents from opening inwardly relative to a wound being dressed.

8. The vented wound dressing barrier of claim 1 wherein the vented wound dressing barrier further comprises one or more synthetic or electrospun fabric layers attached to the one or more membrane layers, the one or more synthetic or electrospun fabric layers having a plurality of vents aligned at least partially with the vents of the one or more membrane layers configured to open with the vents of the one or more membrane layers to allow drainage of fluids from a wound.

9. The vented wound dressing barrier of claim 1 wherein the one or more membrane layers with a plurality of vents are multiple membrane layers of amnion or chorion or combinations of amnion and chorion layers stacked to form a multi-layered laminate.

10. The vented wound dressing barrier of claim 1 wherein the plurality of vents are oriented and arranged in patterns.

11. The vented wound dressing barrier of claim 1 wherein the plurality of vents are oriented in random orientations.

12. The vented wound dressing barrier of claim 1 wherein the plurality of vents are made in random sizes or shapes in the one or more membrane layers.

13. A vented wound dressing barrier comprising:
a vented wound dressing barrier, the vented wound dressing barrier including one or more membrane layers with a plurality of vents, the vents being cut along a perimeter of the vents through the one or more membrane layers and having a connection portion uncut relative to the one or more membrane layers thereby forming a hinge configured to allow the vents to open for drainage when exposed to fluid underlying the vented wound dressing barrier; and
a cryoprotectant coating, the cryoprotectant coating covering the one or membrane layers and wherein the combination of the one or more membrane layers with the cryoprotectant coating are dried or freeze-dried to form a coated vented wound dressing barrier.

14. The vented wound dressing barrier of claim 13 wherein the cryoprotectant is a polyampholyte tissue protectant.

* * * * *